United States Patent [19]

Chao et al.

[11] Patent Number: 4,935,580
[45] Date of Patent: Jun. 19, 1990

[54] PROCESS FOR PURIFICATION OF HYDROCARBONS USING METAL EXCHANGED CLINOPTILOLITE TO REMOVE CARBON DIOXIDE

[75] Inventors: Chien C. Chao, Millwood, N.Y.; Henry Rastelli, New Fairfield, Conn.

[73] Assignee: UOP, Des Plaines, Ill.

[21] Appl. No.: 206,280

[22] Filed: Jun. 14, 1988

[51] Int. Cl.$^5$ .............................................. B01D 53/04
[52] U.S. Cl. ....................................... 585/820; 55/68; 55/74
[58] Field of Search ............... 55/68, 74, 30; 585/820; 208/310 Z

[56] References Cited

U.S. PATENT DOCUMENTS

| 4,515,605 | 5/1985 | Inoue et al. | 55/68 |
| 4,732,584 | 3/1988 | Coe et al. | 55/66 |
| 4,743,276 | 5/1988 | Nishida et al. | 55/68 |
| 4,747,854 | 5/1988 | Maroulis et al. | 55/66 |

OTHER PUBLICATIONS

Methane/Nitrogen Gas Separation over the Zeolite Clinoptilolite by the Selective Adsorption of Nitrogen, Frankiewicz et al., Industrial Gas Separation/American Chemical Society, Chapter 11, 1983.

*Primary Examiner*—Glenn Caldarola
*Attorney, Agent, or Firm*—Thomas K. McBride; Richard G. Miller

[57] ABSTRACT

Clinoptilolites, including both natural clinoptilolites and those which have been ion-exchanged with metal cations such as lithium, sodium, potassium, calcium, magnesium, barium, strontium, zinc, copper, cobalt, iron and manganese, are useful for the removal of traces of carbon dioxide and water from streams of hydrocarbons having kinetic diameters of not more than about 5 Å.

12 Claims, No Drawings

PROCESS FOR PURIFICATION OF HYDROCARBONS USING METAL EXCHANGED CLINOPTILOLITE TO REMOVE CARBON DIOXIDE

FIELD OF THE INVENTION

This invention relates to a process for the purification of hydrocarbons. More specifically, this invention relates to a process for the removal of carbon dioxide and, optionally, water from hydrocarbons using clinoptilolites. The clinoptilolites used may be either natural clinoptilolites or clinoptilolites which have been modified by ion-exchange with one or more of a number of metal cations.

BACKGROUND OF THE INVENTION

It is known that mixtures of molecules having differing sizes and shapes can be separated by contacting the mixture with a molecular sieve into which one component of the mixture to be separated is more strongly adsorbed by the molecular sieve than the other. The strongly adsorbed component is preferentially adsorbed by the molecular sieve and leaves behind outside the molecular sieve a mixture (hereinafter referred to as the "first product mixture") which is enriched in the weakly or non-adsorbed component as compared with the original mixture. The first product mixture is separated from the molecular sieve and the conditions of the molecular sieve varied (typically either the temperature of or the pressure upon the molecular sieve is altered), so that the adsorbed material becomes desorbed, thereby producing a second mixture which is enriched in the adsorbed component as compared with the original mixture.

Whatever the exact details of the apparatus and process steps used in such a process, critical factors include the capacity of the molecular sieve for the more adsorbable components and the selectivity of the molecular sieve (i.e., the ratio in which the components to be separated are adsorbed). In many such processes, zeolites are the preferred adsorbents because of their high adsorption capacity and, when chosen so that their pores are of an appropriate size, their high selectivity.

Most prior art attempts to use zeolites in the separation of gaseous mixtures have been made with synthetic zeolites. Although natural zeolites are readily available at low cost, hitherto the natural zeolites have not been favored as adsorbents because it has been felt that the natural zeolites are not sufficiently consistent in composition to be useful as adsorbents in such processes. However, there are relatively few synthetic zeolites with pore sizes in the range of about 3 to 4 Å, which is the pore size range of interest for a number of potentially important gaseous separations, for example separation of carbon dioxide from methane and other hydrocarbons, including ethylene and propylene, having kinetic diameters not greater than about 5 Å.

As a result of the lack of zeolites having pore sizes in the range of 3 to 4 Å, certain important industrial separations are conducted rather inefficiently. For example, in the manufacture of polyethylene, so-called ethylene streams are produced which contain ethylene, ethane and propane, together with traces (typically of the order of 10 parts per million) of carbon dioxide. It is necessary to lower the already small proportion of carbon dioxide further before the ethylene stream reaches the polymerization reactor, because the presence of even a few parts per million of carbon dioxide poisons commercial ethylene polymerization catalysts. At present, carbon dioxide removal is usually effected by passing the ethylene stream through a bed of calcium zeolite A. Although calcium A zeolite is an efficient adsorber of carbon dioxide, it also adsorbs relatively large quantities of ethylene, and given the much greater partial pressure of ethylene in the ethylene stream, the quantity of ethylene adsorbed is much greater than that of carbon dioxide. Thus, relatively large quantities of ethylene are wasted in the removal of the traces of carbon dioxide. Similar problems are encountered in the propylene stream used to manufacture polypropylene.

Clinoptilolites are a well-known class of natural zeolites which have not hitherto been used extensively for separation of gaseous mixtures, although a few such separations are described in the literature. For example, European patent application No. 4850131.8 (Publication No. 132 239) describes a process for the separation of oxygen and argon using as the adsorbent . raw clinoptilolite (i.e., clinoptilolite which has not been subjected to any ion-exchange).

Industrial Gas Separation (published by the American Chemical Society), Chapter 11, Frankiewicz and Donnell, Methane/Nitrogen Gas Separation over the Zeolite Clinoptilolite by the Selective Adsorption of Nitrogen (1983) describes separation of gaseous mixtures of methane and nitrogen using both raw clinoptilolite and clinoptilolite which had been ion-exchanged with calcium.

It is known that the adsorption properties of many zeolites, and hence their ability to separate gaseous mixtures, can be varied by incorporating various metal cations into the zeolites, typically by ion-exchange or impregnation. For example, U.S. Pat. No. 2,882,243 to Milton describes the use of zeolite A having a silica/alumina ratio of $1.85 \pm 0.5$ and containing hydrogen, ammonium, alkali metal, alkaline earth metal or transition metal cations. The patent states that K A zeolite adsorbs water and excludes hydrocarbons and alcohols, while Ca A zeolite adsorbs straight-chain hydrocarbons but excludes branched-chain and aromatic hydrocarbons.

In most cases, the changes in the adsorption properties of zeolites following ion-exchange are consistent with a physical blocking of the pore opening by the cation introduced; in general, in any given zeolite, the larger the radius of the ion introduced, the smaller the pore diameter of the treated zeolite (for example, the pore diameter of K A zeolite is smaller than that of Na A zeolite), as measured by the size of the molecules which can be adsorbed into the zeolite.

It has now been discovered that clinoptilolites (both natural clinoptilolites and clinoptilolites which have been ion-exchanged with any one or more of a number of metal cations) exhibit adsorption properties which are useful in the separation of carbon dioxide from hydrocarbons. In contrast to most prior art zeolites modified by ion-exchange, the pore sizes, and hence the adsorption properties, of ion-exchanged clinoptilolites are not a simple function of the ionic radius of the exchanged cations.

SUMMARY OF THE INVENTION

This invention provides a process for separating a minor proportion of carbon dioxide from a hydrocarbon having a kinetic diameter of not more than about 5

Å, which process comprises contacting the carbon-dioxide-containing hydrocarbon with a clinoptilolite, thereby causing the carbon dioxide to be selectively adsorbed into the clinoptilolite. If the hydrocarbon also contains water as an impurity, contacting the hydrocarbon with the clinoptilolite will normally remove the water as well as the carbon dioxide. Desirably, the hydrocarbon contains from 1 to 5, preferably 1 to 4, carbon atoms and is an acyclic hydrocarbon.

This invention also provides a process for the production of a modified clinoptilolite wherein at least about 40 percent of the ion-exchangeable cations in the clinoptilolite comprise any one or more of lithium, sodium, potassium, calcium, magnesium, barium, strontium, zinc, copper, cobalt, iron and manganese cations, said process comprising subjecting a clinoptilolite to ion-exchange with a solution containing sodium cations until at least about 40 percent of the ion-exchangeable non-sodium cations in the clinoptilolite have been replaced by sodium cations, thereby producing a sodium clinoptilolite, and thereafter subjecting said sodium clinoptilolite to ion-exchange with a solution containing any one or more of lithium, sodium, potassium, calcium, magnesium, barium, strontium, zinc, copper, cobalt, iron and manganese cations.

DETAILED DESCRIPTION OF THE INVENTION

As already mentioned, this invention provides a process for separating a minor proportion of carbon dioxide from a hydrocarbon having a kinetic diameter of not more than about 5 Å, which process comprises contacting the carbon-dioxide-containing hydrocarbon with a clinoptilolite. The clinoptilolites used in the process of the present invention may be natural clinoptilolites. However, being natural materials, clinoptilolites are variable in composition; chemical analysis shows that the cations in clinoptilolite samples from various mines vary widely. Moreover, natural clinoptilolites frequently contain substantial amounts of impurities, especially soluble silicates, which may cause difficulties in the aggregation or pelletization of the clinoptilolite (discussed in more detail below), or may cause undesirable side-effects which would inhibit practicing this invention.

Accordingly, before being used in the process of the present invention, it is preferred that the clinoptilolites be modified by ion-exchange with at least one metal cation. Among the cations which can usefully be ion-exchanged into clinoptilolites are lithium, sodium, potassium, magnesium, calcium, strontium, barium, zinc, copper, cobalt, iron and manganese cations. Desirably, the ion-exchange is continued until at least about 40 percent of the cations in the natural clinoptilolite have been replaced by one or more of these cations. The preferred metal cations for treatment of the clinoptilolites used in the process of the present invention are lithium, sodium, calcium, magnesium, barium and strontium cations, with sodium being especially preferred. When sodium is used as the ion-exchange metal cation, it is preferred that the ion-exchange be continued until at least about 60 percent of the total cations in the clinoptilolite are replaced by sodium cations.

Since clinoptilolite is a natural material, the particle sizes of the commercial product varies, and the particle size of the clinoptilolite may affect the speed and completeness of the ion-exchange reaction. In general, it is recommended that the particle size of the clinoptilolite used in the ion-exchange reaction be not greater than about 8 U.S. mesh. Although the particle sizes of many commercial clinoptilolites are greater, their particle sizes are readily reduced by grinding or other techniques which will be familiar to those skilled in the ion-exchange of molecular sieves.

Techniques for the ion-exchange of zeolites such as clinoptilolite are well-known to those skilled in the molecular sieve art, and hence will not be described in detail herein. In the ion-exchange, the cation is conveniently present in the solution in the form of its chloride. It is desirable that the ion-exchange be continued until at least about 40 percent, and preferably at least about 60 percent, of the cations in the original clinoptilolite have been replaced, and in most cases it is convenient to continue the ion-exchange until no further amount of the desired cation can easily be introduced into the clinoptilolite. To secure maximum replacement of the original clinoptilolite cations, it is recommended that the ion-exchange be conducted using a solution containing a quantity of the cation to be introduced which is from about 2 to about 100 times the ion-exchange capacity of the clinoptilolite. Typically the ion-exchange solution will contain from about 0.1 to about 5 moles per liter of the cation, and will be contacted with the original clinoptilolite for at least about 1 hour. The ion-exchange may be conducted at ambient temperature, although in many cases carrying out the ion-exchange at elevated temperatures, usually less than 100° C., accelerates the ion-exchange process.

Since clinoptilolite is a natural material of variable composition, the cations present in the raw clinoptilolite vary, although typically the cations include a major proportion of alkali metals. It is typically found that, even after the most exhaustive ion-exchange, a proportion of the original clinoptilolite cations can not be replaced by other cations. However, the presence of this small proportion of the original clinoptilolite cations does not interfere with the use of the ion-exchanged clinoptilolites in the process of the present invention.

Any of the modified clinoptilolites of the present invention can be prepared directly by ion-exchange of natural clinoptilolite with the appropriate cation. However, in practice such direct ion-exchange may not be the most economical or practical technique. Being natural minerals, clinoptilolites are variable in composition and frequently contain substantial amounts of impurities, especially soluble silicates. To ensure as complete an ion-exchange as possible, and also to remove impurities, it is desirable to effect the ion-exchange of the clinoptilolite using a large excess of the cation which it is desired to introduce. However, if, for example, a large excess of barium is used in such an ion-exchange, the disposal and/or recovery of barium from the used ion-exchange solution presents a difficult environmental problem, in view of the limitations on release of poisonous barium salts into the environment. Furthermore, some impurities, including some silicates, which are removed in a sodium ion-exchange are not removed in a barium ion-exchange because the relevant barium compounds are much less soluble than their sodium counterparts.

In addition, when the modified clinoptilolites of the present invention are to be used in industrial adsorbers, it may be preferred to aggregate (pelletize) the modified clinoptilolite to control the macropore diffusion, or else in an industrial size adsorption column pulverulent clinoptilolite may compact, thereby blocking, or at least significantly reducing flow through, the column. Those skilled in molecular sieve technology are aware of conventional techniques for aggregating molecular sieves; such techniques usually involve mixing the molecular sieve with a binder, which is typically a clay, forming the mixture into an aggregate, typically by extrusion or bead formation, and heating the formed molecular sieve/clay mixture to a temperature of about 600–700° C. to convert the green aggregate into one which is resistant to crushing.

The binders used to aggregate the clinoptilolites may include clays, silicas, aluminas, metal oxides and mixtures thereof. In addition, the clinoptilolites may be formed with materials such as silica, alumina, silica-alumina, silica-magnesia, silica-zirconia, silica-thoria, silica-berylia, and silica-titania, as well as ternary compositions, such as silica-alumina-thoria, silica-alumina-zirconia and clays present as binders. The relative proportions of the above materials and the clinoptilolites may vary widely with the clinoptilolite content ranging between about 1 and about 99 percent by weight of the composite. Where the clinoptilolite is to be formed into aggregates prior to use, such aggregates are desirably about 1 to about 4 mm. in diameter.

Although the ion-exchange(s) needed to produce the modified clinoptilolites of this invention may be conducted either before or after aggregation, it is often inadvisable to subject raw clinoptilolite to the process of conversion to the aggregate, since various impurities may be affected by the heat required for aggregation and may interfere with the formation of aggregates. However, in some cases, it may also be desirable to avoid subjecting some modified clinoptilolites of the invention to the heat required for aggregation, since certain of these modified clinoptilolites are affected by heat, as discussed in more detail below.

To avoid the aforementioned difficulties, it is generally preferred to produce modified clinoptilolites of the present invention other than sodium clinoptilolite by first subjecting raw clinoptilolite to a sodium ion-exchange, aggregating the sodium clinoptilolite thus produced, and then effecting a second ion-exchange on the aggregated material to introduce the desired non-sodium cations. When a sodium clinoptilolite itself is to be used, it is in general not necessary to carry out a second sodium ion-exchange after aggregation; the aggregated sodium clinoptilolite may be used without further processing and gives satisfactory results, which do not appear to be significantly improved by a second ion-exchange.

Before being used in the processes of the present invention, the clinoptilolites need to be activated by heating. If the clinoptilolite is aggregated as discussed above, the heat required for aggregation will normally be sufficient to effect activation also, so that no further heating is required. If, however, the clinoptilolite is not to be aggregated, a separate activation step will usually be required. Sodium clinoptilolite can be activated by heating in air or vacuum to approximately 350° C. for about 1 hour. The temperature needed for activation of any specimen of clinoptilolite is easily determined by routine empirical tests which pose no difficulty to those skilled in molecular sieve technology.

If the non-sodium modified clinoptilolites are produced by the preferred process discussed above, in which a raw clinoptilolite is first sodium ion-exchanged, the resultant sodium clinoptilolite aggregated, and finally the aggregated sodium clinoptilolite is ion-exchanged with the desired cation, it is normally necessary to effect a second activation of the final product; however, the activation temperature required is not as high as that required for aggregation, and consequently one avoids exposing the non-sodium clinoptilolite to aggregation temperatures. As already indicated, in some cases it is desirable to limit the temperatures to which some of the non-sodium clinoptilolites of the present invention are exposed since exposure of the modified clinoptilolite to excessive temperatures may cause structural damage of the clinoptilolite which may render it less effective in the process of the present invention.

The process of the present invention is primarily intended for removal of traces of carbon dioxide from hydrocarbons, especially ethylene streams (comprising mainly ethylene and ethane) such as those used in the production of polyethylene (and the corresponding propylene streams, comprising mainly propylene and propane, such as those used in the manufacture of polypropylene), where the presence of even a few parts per million of carbon dioxide causes severe poisoning of the polymerization catalyst. In such streams, the carbon dioxide content of the gas is normally not greater than about 200 parts per million, and the carbon dioxide partial pressure not greater than about 20 Torr. As already mentioned, sodium clinoptilolite is the preferred material for this process. The same process will remove any water which may be present in the hydrocarbon stream, and this removal of water is also desirable since water, even in very small amounts, is active as a polymerization catalyst poison.

The present process may also be useful for the separation of carbon dioxide from methane or other hydrocarbons for use in a process such as steam reforming. The present invention may also be used to separate carbon dioxide from butanes and butenes, or even larger hydrocarbons (for example n-hexane) which have kinetic diameters not greater than about 5 Å.

Since these types of processes involve the separation of minor amounts of carbon dioxide (and optionally water) impurity from much larger amounts of hydrocarbons, they may be effected in the conventional manner by simply passing the hydrocarbon stream through a bed of the clinoptilolite, which is normally in aggregate form. As the operation of the process continues, there develops in the bed a so-called "front" between the clinoptilolite loaded with carbon dioxide and clinoptilolite not so loaded, and this front moves through the bed in the direction of gas flow. Before the front reaches the downstream end of the bed (which would allow impure hydrocarbon gas to leave the bed), the bed is regenerated by cutting off the flow of hydrocarbon gas and passing through the bed a purge gas which causes desorption of the carbon dioxide (and water, if any is present) from the bed. In industrial practice, the purge gas is typically nitrogen or natural gas heated to a temperature in the range of 50°–350° C., and such a purge gas is also satisfactory in the processes of the present invention.

A nitrogen purge operation leaves the bed loaded with nitrogen. To remove this nitrogen, it is only necessary to pass one or two bed volumes of the hydrocarbon stream through the bed; the resultant gas leaving the bed is mixed with nitrogen and should normally be discarded. The loss of gas resulting from such discarding is negligible, since the purging and subsequent removal of nitrogen only require to be performed after the passage of hundreds or thousands of bed volumes of impure hydrocarbon.

If the process of the present invention is to be used to separate carbon dioxide from hydrocarbons containing larger amounts of carbon dioxide (of the order of 10 percent), other conventional pressure swing adsorption and temperature swing adsorption techniques may be used. Such techniques are well-known to those skilled in molecular sieve technology; see, for example, U.S. Pat. Nos.:
3,430,418
3,738,087
3,986,849
4,398,926
4,589,888 and
4,723,966,
and British Pat. No. 1,536,995.

It should be noted that the change in pore size of the clinoptilolite after ion-exchange is not a simple function of the ionic radius of the cation introduced. It has been determined empirically, by measuring the adsorption of variously sized gas molecules into ion-exchanged clinoptilolites, that the order of pore sizes in such clinoptilolites is:

CaClino < NaClino < LiClino < MgClino
< ZnClino < KClino < SrClino < BaClino where "Clino" represents the clinoptilolite lattice framework. Since calcium and magnesium cations have ionic radii smaller than strontium and barium cations, and since sodium and lithium cations have ionic radii smaller than potassium cations, increase in radius of ion-exchanged cation does not always correlate with decrease in pore size of the clinoptilolite, and thus, unlike many other zeolites, the change in pore size of ion-exchanged clinoptilolites cannot be a simple matter of pore blocking.

Although ion-exchange of clinoptilolite does produce a modified clinoptilolite having a consistent pore size, the exact pore size depends not only upon the metal cation(s) exchanged but also upon the thermal treatment of the product following ion-exchange. In general, there is a tendency for the pore size of the modified clinoptilolites of this invention to decrease with exposure to increasing temperature. Accordingly, in selecting an activation temperature for the modified clinoptilolites, care should be taken not to heat modified clinoptilolites to temperatures which cause reductions in pore size so severe as to adversely affect the performance of the modified clinoptilolite in the process of the present invention.

Although the behavior of the modified clinoptilolites on exposure to heat does limit the activation temperatures which can be employed, the thermal reduction in pore size does offer the possibility of "fine tuning" the pore size of a modified clinoptilolite to optimize its performance in the process of the present invention.

The following Examples are given, though by way of illustration only, to show preferred processes of the present invention. All adsorption measurements are at 23° C. unless otherwise stated. Furthermore, all separation factors given in the form "Separation factor X/Y"

are calculated by:

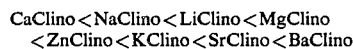

where $P_x$ and $P_y$ are the pressures of components X and Y respectively and $L_X$ and $L_Y$ are the corresponding loadings of X and Y in millimoles per gram of adsorbent.

EXAMPLES

Example 1: Natural Clinoptilolites

Seven different samples of commercially-available clinoptilolites were used in these experiments and as starting materials for the preparation of some of the modified clinoptilolites prepared in the later Examples. The chemical analyses of these clinoptilolites are shown in Table 1 below, while carbon dioxide and ethane separation data are shown in Table 2. For comparison, Table 2 includes data for zeolite 5A, a commercial material used for gas separations.

TABLE 1

| Component (wt. percent) | Clinoptilolite | | | | | | |
|---|---|---|---|---|---|---|---|
| | A | B | C | D | E | F | G |
| Loss on ignition | 12.6 | 15.2 | 13.2 | 11.6 | 13.6 | 13.8 | 13.3 |
| Al$_2$O$_3$ (anhydrous) | 14.188 | 12.618 | 12.903 | 12.670 | 13.426 | 13.573 | 13.379 |
| SiO$_2$ (anhydrous) | 72.883 | 75.236 | 76.152 | 75.924 | 75.964 | 74.710 | 75.779 |
| Na$_2$O (anhydrous) | 3.547 | 2.252 | 4.090 | 3.801 | 3.831 | 3.840 | 3.656 |
| K$_2$O (anhydrous) | 1.796 | 2.170 | 4.078 | 4.355 | 2.280 | 2.541 | 1.984 |
| MgO (anhydrous) | 1.796 | 2.123 | 0.325 | 0.575 | 0.714 | 1.044 | 0.734 |
| CaO (anhydrous) | 3.341 | 2.724 | 1.039 | 1.403 | 1.887 | 2.390 | 2.434 |
| SrO (anhydrous) | 0.049 | 0.018 | — | 0.032 | 0.345 | 0.563 | 0.406 |
| BaO (anhydrous) | 0.135 | 0.051 | — | 0.376 | 0.071 | 0.246 | 0.248 |
| Fe$_2$O$_3$ (anhydrous) | 2.208 | 3.054 | 0.919 | 0.989 | 1.262 | 1.508 | 1.292 |

TABLE 2

| Adsorption (wt. percent) | Clinoptilolite | | | | | | | |
|---|---|---|---|---|---|---|---|---|
| | A | B | C | D | E | F | G | 5A |
| CO$_2$, 5 Torr, 3 hours | 5.1 | 5.6 | 6.8 | 6.1 | 5.8 | 4.9 | 6.4 | 8.2 |
| C$_2$H$_4$, 700 Torr | 0.981 | 2.177 | 0.990 | 0.904 | 1.453 | 1.098 | 2.222 | 7.700 |

TABLE 2-continued

| Adsorption | Clinoptilolite | | | | | | | |
|---|---|---|---|---|---|---|---|---|
| (wt. percent) | A | B | C | D | E | F | G | 5A |
| 3 hours Separation factor $CO_2/C_2H_4$ | 463 | 229 | 612 | 601 | 356 | 398 | 257 | 95 |

From the data in Table 2, it will be seen that all the seven clinoptilolite specimens had carbon dioxide/ethane separation factors substantially better than that of zeolite 5A.

Example 2: Sodium clinoptilolite

1500 Gm. (dry weight) of clinoptilolite C in Example 1 was ground to 30×50 U.S. mesh and placed in a jacketed glass column. The column was heated to 80° C. by passing oil through the jacket, and 30 liters of 1.86 N sodium chloride solution was passed through the column at a flow rate of 19 ml/minute for 16 hours. The clinoptilolite was then washed by passing distilled water through the column, and dried in air at ambient temperature.

The sodium clinoptilolite thus produced was subjected to chemical analysis and its adsorption properties were measured using a McBain quartz spring balance. Before being used in the adsorption tests, the sodium clinoptilolite was activated by heating to 375° C. under vacuum for one hour.

Part of the sodium clinoptilolite was then subjected to a second sodium ion-exchange. 200 Grams of the sodium clinoptilolite were treated in the same column as before by passing 9 liters of 0.5 M sodium chloride solution over the clinoptilolite for 16 hours. The chemical analysis and adsorption properties of the doubly-exchanged sodium clinoptilolite were then measured in the same manner as before.

The chemical analyses of both sodium clinoptilolites are shown in Table 3 below, and their adsorption properties are shown in Table 4, along with those of 5A zeolite; in both cases, the singly-exchanged material is designated "NaClino", while the doubly-exchanged material is designated "NaNaClino". For comparative purposes, the chemical analysis and adsorption data for the clinoptilolite C starting material (given in Tables 1 and 2 above) are repeated in Tables 3 and 4.

TABLE 3

| Component (wt. percent) | NaClino | NaNaClino | Clino C |
|---|---|---|---|
| Loss on ignition | 13.3 | 14.5 | 13.2 |
| $Al_2O_3$ (anhydrous) | 13.033 | 12.982 | 12.903 |
| $SiO_2$ (anhydrous) | 79.123 | 78.246 | 76.152 |
| $Na_2O$ (anhydrous) | 6.332 | 6.199 | 4.090 |
| $K_2O$ (anhydrous) | 1.465 | 0.750 | 4.078 |
| MgO (anhydrous) | 0.219 | — | 0.325 |
| CaO (anhydrous) | 0.276 | 0.199 | 1.039 |
| $Fe_2O_3$ (anhydrous) | 0.980 | — | 0.919 |

TABLE 4

| Adsorption (wt. percent) | NaClino | NaNaClino | Clino C | 5A |
|---|---|---|---|---|
| $CO_2$, 5 Torr, 3 hours | 5.4 | 5.2 | 6.8 | 8.2 |
| $CH_4$, 700 Torr, 3 hours | 0.100 | 0.100 | — | — |
| Separation factor $CO_2/CH_4$ | 2749 | 2647 | — | 380 |
| Water, 4.7 Torr | — | 5.4 | — | 23.0 |
| Separation factor $H_2O/CH_4$ | — | 17848 | — | 2768 |
| $C_2H_6$, 50 Torr 3 hours | 0.100 | 0.100 | — | 3.1 |
| Separation factor $H_2O/C_2H_6$ | — | 2390 | — | 132 |
| Separation factor $CO_2/C_2H_6$ | 368 | 354 | — | 18 |
| $C_2H_4$, 50 Torr 3 hours | 0.300 | 0.200 | — | 4.8 |
| Separation factor $H_2O/C_2H_4$, 50 Torr | — | 1116 | — | 165 |
| Separation factor $CO_2/C_2H_4$, 50 Torr | 115 | 166 | — | 11 |
| $C_2H_4$, 700 Torr 3 hours | — | 0.507 | 0.990 | 7.7 |
| Separation factor $H_2O/C_2H_4$, 700 Torr | — | 2374 | — | 692 |
| Separation factor $CO_2/C_2H_4$, 700 Torr | — | 879 | 612 | 95 |

From the data in Tables 3 and 4, it will be seen that both the singly and doubly-exchanged sodium clinoptilolites would be useful for the separation of carbon dioxide and water from hydrocarbon gas streams, that both are superior to the untreated Clinoptilolite C for this purpose, and that all three of the clinoptilolites are much better than 5A zeolite. The second sodium ion-exchange does not appreciably increase the sodium content of the clinoptilolite, but does reduce the potassium and calcium contents. However, since the second sodium ion-exchange does not appreciably increase the relevant separation factors, in general a single sodium ion-exchange would be sufficient to provide a material suitable for use in the process of the present invention.

Example 3: Potassium clinoptilolite

200 Gm. (dry weight) of the singly-exchanged sodium clinoptilolite prepared in Example 2 was placed in a jacketed glass column. The column was heated to 80° C. by passing oil through the jacket, and 9 liters of 0.5 N potassium chloride solution was passed through the column at a flow rate of 9 ml/minute for 16 hours. The clinoptilolite was then washed by passing distilled water through the column, and dried in air at ambient temperature.

The potassium clinoptilolite thus produced was subjected to chemical analysis and its adsorption properties were measured using a McBain quartz spring balance. Before being used in the adsorption test, the potassium clinoptilolite was activated by heating to 375° C. under vacuum for one hour. The results are shown in Tables 5 and 6 below.

TABLE 5

| Component (wt. percent) | KClino |
|---|---|
| Loss on ignition | 12.4 |
| $Al_2O_3$ (anhydrous) | 12.982 |
| $SiO_2$ (anhydrous) | 76.027 |
| $Na_2O$ (anhydrous) | 0.251 |
| $K_2O$ (anhydrous) | 10.526 |
| MgO (anhydrous) | — |
| CaO (anhydrous) | 0.148 |

TABLE 6

| Adsorption (wt. percent) | KClino |
|---|---|
| $CO_2$, 5 Torr, 3 hours | 5.4 |
| $CH_4$, 700 Torr, 3 hours | 1.1 |
| Separation factor $CO_2/CH_4$ | 250 |
| Water, 4.7 Torr | 11.0 |
| Separation factor $H_2O/CH_4$ | 1324 |
| $C_2H_6$, 50 Torr 3 hours | 2.3 |
| Separation factor $H_2O/C_2H_6$ | 85 |
| Separation factor $CO_2/C_2H_6$ | 16 |
| $C_2H_4$, 50 Torr 3 hours | 2.2 |
| Separation factor $H_2O/C_2H_4$ | 83 |
| Separation factor $CO_2/C_2H_4$ | 16 |

These results indicate that the potassium clinoptilolite was able to separate carbon dioxide and water from hydrocarbon streams, but that its relevant separation factors were lower than those of the natural clinoptilolite from which it is derived or those of the sodium clinoptilolites prepared in Example 2 above.

These adsorption results also demonstrate that, contrary to what would be expected on the basis of the ionic radii of the cations involved ($Na^+$ has a Pauling ionic radius of 0.95 Å, while $K^+$ has a Pauling ionic radius of 1.33 Å), the potassium clinoptilolite has a substantially greater pore size than the sodium clinoptilolite. Accordingly, the pore size of a modified clinoptilolite of this invention cannot be predicted from a knowledge of the ionic radius of the cation introduced and the normal pore blocking mechanism which is typical of the zeolites, and thus the cation must affect the pore size of the clinoptilolite by some mechanism other than simple physical pore blocking.

Example 4: Separation of carbon dioxide from ethylene streams using zeolite 5A and sodium clinoptilolite A column 1 inch internal diameter by 5 feet was filled with zeolite 5A (a commercial product sold by Union Carbide Corporation) in the form of pellets 1/16 inch in diameter. An ethylene feed stream containing from 15 to 70 parts per million by volume of carbon dioxide was passed through the column at 525 psig. and 90° F. at a flow rate of 70 standard cubic feet per hour. The effluent from the column was initially free from carbon dioxide; however, after 6.9 hours of operation, carbon dioxide began to appear in the effluent and reached a concentration of 10 percent of its concentration in the feed. At an average carbon dioxide concentration in the feed of 45 parts per million by volume, the equilibrium carbon dioxide loading of the zeolite was 0.31 weight percent.

A sodium clinoptilolite was prepared by a single ion-exchange of a clinoptilolite with sodium chloride. The sodium clinoptilolite has formed into 1/16 inch pellets using 5 percent by weight Avery clay binder, and tested for its ability to remove carbon dioxide from the ethylene feed stream under the same conditions as described for zeolite 5A. Breakthrough of carbon dioxide occurred only after 43 hours of operation, and at an average carbon dioxide concentration in the feed of 46 parts per million by volume, the equilibrium carbon dioxide loading of the clinoptilolite was 1.63 weight percent, 5.3 times the equilibrium loading of the 5A zeolite. Thus, the sodium clinoptilolite was greatly superior to the 5A zeolite in removing carbon dioxide from the ethylene feed stream.

Examples 5-18: Adsorption properties of various modified clinoptilolites

A number of modified clinoptilolites were prepared in substantially the same way as in Example 2 above, and their adsorption properties were determined using the McBain spring balance, in some cases after pelletization with clay. The methods of preparation are summarized in Table 7 below; in the column headed "Starting Material", "Clino A" etc refers to the natural clinoptilolites described in Example 1 above, while "NaClino" refers to the singly-exchanged material produced in Example 2 above. A "—" in the column headed "Binder" indicates that the modified clinoptilolite was not pelletized before the adsorption measurements were made. Chemical analyses of the modified clinoptilolites are given in Table 8 and adsorption data in Table 9. All adsorption measurements were taken at 23° C. A prime (') following the Clinoptilolite letter indicates material from the same deposit as the corresponding clinoptilolite in Example 1 above, but from a different lot of ore.

TABLE 7

| Ex. # | Starting Material | Ion-exchange solution | Binder |
|---|---|---|---|
| 5 | NaClino | 0.4 M LiCl 100 × excess | — |
| 6 | NaClino | 0.2 M $MgCl_2$ 20 × excess | — |
| 7 | NaClino | 0.25 M $CaCl_2$ 10 × excess | — |
| 8 | NaClino | 0.25 M $BaCl_2$ 10 × excess | — |
| 9 | NaClino | 0.2 M $ZnCl_2$ 100 × excess | — |
| 10 | Clino E' | As Example 2 | — |
| 11 | Clino E' | 0.2 M KCl 20 × excess | — |
| 12 | Clino E' | 1 M $MgCl_2$ 12 × excess | 5% Avery clay |
| 13 | Clino E | 0.3 M $BaCl_2$ 10 × excess | — |
| 14 | Clino E' | 0.3 M $BaCl_2$ 10 × excess | 5% Avery clay |
| 15 | Clino A' | As Example 2 | — |
| 16 | Clino A' | KCl, 100 × excess | — |
| 17 | Clino B' | As Example 2 | — |
| 18 | Clino B' | KCl, 100 × excess | — |

TABLE 8

| Component (wt. percent) | Example # | | | | | | | | | | | | | |
|---|---|---|---|---|---|---|---|---|---|---|---|---|---|---|
| | 5 | 6 | 7 | 8 | 9 | 10 | 11 | 12 | 13 | 14 | 15 | 16 | 17 | 18 |
| Loss on ignition | 13.9 | 14.4 | 14.8 | 14.2 | 13.8 | 13.1 | 11.5 | 11.2 | 11.9 | 9.6 | 13.6 | 11.3 | 12.1 | 10.0 |
| $Al_2O_3$ (anhydrous) | 13.473 | 13.201 | 13.263 | 12.354 | 12.529 | 13.234 | 12.768 | 14.752 | 12.032 | 15.044 | 12.847 | 12.627 | 14.790 | 14.111 |
| $SiO_2$ (anhydrous) | 81.185 | 80.140 | 78.286 | 74.476 | 75.638 | 76.180 | 72.768 | 75.450 | 70.715 | 71.018 | 76.968 | 75.862 | 72.696 | 71.444 |
| $Na_2O$ (anhydrous) | 0.269 | 2.687 | 0.263 | 0.350 | 0.309 | 6.145 | 0.546 | 2.950 | 0.603 | 0.754 | 7.141 | 0.135 | 7.258 | 0.744 |
| $K_2O$ (anhydrous) | 1.069 | 1.554 | 0.947 | 1.049 | 1.636 | 1.542 | 10.282 | 2.601 | 0.860 | 1.041 | 0.271 | 11.612 | 0.964 | 11.333 |
| MgO (anhydrous) | 0.228 | 2.605 | 0.224 | — | 0.194 | 0.458 | 0.253 | 2.061 | 0.444 | 0.704 | 0.223 | 0.265 | 0.784 | 0.839 |
| CaO (anhydrous) | 0.497 | 0.266 | 6.573 | 0.350 | 0.527 | 0.486 | 0.397 | 0.657 | 0.763 | 1.294 | 1.458 | 1.364 | 0.975 | 0.868 |
| BaO (anhydrous) | — | — | — | — | 2.877 | 0.265 | 0.181 | 0.372 | 13.053 | 11.173 | — | — | — | — |
| $Fe_2O_3$ (anhydrous) | 0.868 | 0.847 | 0.805 | — | 0.765 | 1.022 | 1.127 | 1.318 | 1.000 | 1.173 | 0.949 | 0.964 | 1.786 | 1.856 |
| Other | 3.287 $Li_2O$ | — | — | 7.226 SrO | 5.487 ZnO | — | — | — | — | — | — | — | — | — |

TABLE 9

| Adsorption Weight percent | Example # | | | | | | | | | |
|---|---|---|---|---|---|---|---|---|---|---|
| | 5 | 6 | 7 | 9 | 10 | 11 | 15 | 16 | 17 | 18 |
| $CO_2$, 5 Torr, 3 hours | 6.42 | 5.54 | 2.69 | 4.67 | 5.51 | 4.60 | 5.56 | 5.16 | 4.36 | 4.73 |
| $CH_4$, 700 Torr, 3 hours | 0.42 | 0.90 | 0.09 | 1.56 | 0.47 | 1.38 | 0.30 | 1.33 | 0.12 | 1.25 |
| Separation factor $CO_2/CH_4$ | 778 | 313 | 1522 | 152 | 599 | 170 | 944 | 198 | 1850 | 193 |
| Water, 4.7 Torr | 13.962 | 13.943 | 12.600 | 13.067 | — | — | — | — | — | — |
| Separation factor $H_2O/CH_4$ | 4401 | 2051 | 18534 | 1109 | — | — | — | — | — | — |
| $C_2H_6$, 50 Torr, 3 hours | 0.48 | 0.33 | 0.10 | 1.76 | — | — | 0.46 | 2.65 | 0.37 | 2.59 |
| Separation factor $H_2O/C_2H_6$ | 515 | 749 | 2234 | 132 | — | — | — | — | — | — |
| Separation factor $CO_2/C_2H_6$ | 91 | 114 | 183 | 18 | — | — | 82 | 13 | 80 | 13 |
| $C_2H_4$, 50 Torr, 3 hours | 0.99 | 0.82 | 0.03 | 2.83 | — | — | 1.06 | 2.95 | 0.55 | 3.15 |
| Separation factor $H_2O/C_2H_4$ | 233 | 281 | 6950 | 76 | — | — | — | — | — | — |
| Separation factor $CO_2/C_2H_4$ | 4.1 | 43 | 571 | 11 | — | — | 33 | 11 | 50 | 10 |

The above data show that the modified clinoptilolites strongly adsorb carbon dioxide and water but have low adsorptions of methane, ethylene and ethane, so that these clinoptilolites are useful for separating carbon dioxide and water from hydrocarbon streams. The potassium and zinc clinoptilolites are comparable to zeolite 5A in their ability to effect these separations (see the data for zeolite 5A in Table 4 above), while the other modified clinoptilolites have separation factors much better than zeolite 5A, and should thus provide better selectivity for the separation of carbon dioxide and water from methane, ethane, and ethylene. Sodium clinoptilolite is superior to potassium clinoptilolite independent of the source of the ore.

We claim:

1. A process for separating a minor proportion of carbon dioxide from a hydrocarbon having a kinetic diameter of not more than about 5A, which process comprises contacting the carbon dioxide-containing mixture with a natural clinoptilolite that has been subjected to ion-exchange with at least one metal cation of the group consisting of lithium, sodium, potassium, calcium, magnesium, barium and strontium cations, thereby causing the carbon dioxide to be selectively adsorbed into the clinoptilolite.

2. A process according to claim 1 wherein the metal cation is sodium.

3. A process according to claim 1 wherein the ion-exchange is continued until at least about 60 percent of the total cations in the natural clinoptilolite are replaced by sodium cations.

4. A process according to claim 1 which is conducted at a temperature in the range of from −15 to +60° C.

5. A process according to claim 1 wherein the carbon dioxide content of the hydrocarbon is not greater than about 200 parts per million.

6. A process according to claim 1 wherein the carbon dioxide partial pressure in the carbon-dioxide-containing hydrocarbon is not greater than about 20 Torr.

7. A process according to claim 1, wherein the hydrocarbon is an acyclic hydrocarbon containing not more than 5 carbon atoms.

8. A process according to claim 7, wherein the hydrocarbon is an acyclic hydrocarbon containing not more than 4 carbon atoms.

9. A process according to claim 8 wherein the hydrocarbon comprises at least one of methane, ethylene, ethane, propylene, propane, a butane and a butene.

10. A process according to claim 9 wherein the hydrocarbon comprises at least one of ethylene, ethane, propylene and propane.

11. A process according to claim 10 wherein the hydrocarbon comprises ethylene.

12. A process according to claim 11 wherein the clinoptilolite is a sodium clinoptilolite.

* * * * *